(12) United States Patent
Shimizu

(10) Patent No.: US 12,307,792 B2
(45) Date of Patent: May 20, 2025

(54) ABNORMAL PHYSICAL CONDITION DETERMINATION SYSTEM, ABNORMAL PHYSICAL CONDITION DETERMINATION METHOD, AND COMPUTER PROGRAM

(71) Applicant: NEC Corporation, Tokyo (JP)

(72) Inventor: Yuta Shimizu, Tokyo (JP)

(73) Assignee: NEC CORPORATION, Tokyo (JP)

( * ) Notice: Subject to any disclaimer, the term of this patent is extended or adjusted under 35 U.S.C. 154(b) by 351 days.

(21) Appl. No.: 17/781,586

(22) PCT Filed: Dec. 4, 2019

(86) PCT No.: PCT/JP2019/047514
§ 371 (c)(1),
(2) Date: Jun. 1, 2022

(87) PCT Pub. No.: WO2021/111567
PCT Pub. Date: Jun. 10, 2021

(65) Prior Publication Data
US 2023/0005279 A1  Jan. 5, 2023

(51) Int. Cl.
*G06K 9/00* (2022.01)
*B60W 40/08* (2012.01)
(Continued)

(52) U.S. Cl.
CPC .......... *G06V 20/597* (2022.01); *B60W 40/08* (2013.01); *F16C 32/0465* (2013.01);
(Continued)

(58) Field of Classification Search
CPC . G06T 2207/30201; G06T 2207/30268; G06T 7/73; G06V 10/62; G06V 10/74; G06V 20/597; G06V 40/171
See application file for complete search history.

(56) References Cited

U.S. PATENT DOCUMENTS 11,404,075 B1 * 8/2022 Lakhani ................. G10L 25/51
11,919,522 B2 * 3/2024 Yamauchi .............. G06V 20/56
(Continued)

FOREIGN PATENT DOCUMENTS

EP  3484874 A1     6/2019
EP  3494874 A1 *  6/2019  ......... A61B 5/02405
(Continued)

OTHER PUBLICATIONS

JP Office Communication for JP Application No. 2023-092541, mailed on Apr. 30, 2024 with English Translation.
(Continued)

*Primary Examiner* — Avinash Yentrapati

(57) ABSTRACT

An abnormal physical condition determination system includes: an extraction unit that extracts a plurality of feature quantities indicating a condition of a target person from an image of the target person; an accumulation unit that accumulates the plurality of feature quantities as time series data; a calculation unit that calculates a relationship between each feature quantity from the plurality of feature quantities accumulated in the accumulation unit; and a determination unit that determines an abnormal physical condition of the target person on the basis of the relationship. According to such an abnormal physical condition determination system, it is possible to appropriately determine the abnormal physical cal condition of the target person.

10 Claims, 14 Drawing Sheets

(51) Int. Cl.
*F16C 32/04* (2006.01)
*F25B 31/02* (2006.01)
*G06T 7/73* (2017.01)
*G06V 10/62* (2022.01)
*G06V 10/74* (2022.01)
*G06V 20/59* (2022.01)
*G06V 40/16* (2022.01)
*B60W 60/00* (2020.01)

(52) U.S. Cl.
CPC ............ *F25B 31/026* (2013.01); *G06T 7/73* (2017.01); *G06V 10/62* (2022.01); *G06V 10/74* (2022.01); *G06V 40/171* (2022.01); *B60W 60/0016* (2020.02); *B60W 2420/403* (2013.01); *B60W 2540/223* (2020.02); *G06T 2207/30201* (2013.01); *G06T 2207/30268* (2013.01)

(56) References Cited

U.S. PATENT DOCUMENTS

| | | | |
|---|---|---|---|
| 2014/0121927 A1* | 5/2014 | Hanita | B60T 7/12 701/70 |
| 2017/0124383 A1 | 5/2017 | Ohbitsu | |
| 2019/0110729 A1* | 4/2019 | Yamataka | A61B 5/1495 |
| 2019/0135325 A1* | 5/2019 | Lisseman | B60W 10/20 |
| 2020/0249764 A1* | 8/2020 | Page | G06V 10/82 |
| 2020/0334477 A1* | 10/2020 | Aoi | A61B 5/11 |
| 2020/0337623 A1* | 10/2020 | Bulut | A61B 5/7275 |
| 2020/0385025 A1 | 12/2020 | Nishimura et al. | |
| 2021/0031789 A1 | 2/2021 | Moriura et al. | |
| 2022/0076039 A1* | 3/2022 | Li | G06F 18/253 |
| 2022/0313132 A1* | 10/2022 | Tsujikawa | A61B 5/4809 |

FOREIGN PATENT DOCUMENTS

| | | |
|---|---|---|
| JP | 2004-301692 A | 10/2004 |
| JP | 2006-034576 A | 2/2006 |
| JP | 2015-141099 A | 8/2015 |
| JP | 2006-040055 A | 3/2016 |
| JP | 2018-160136 A | 10/2018 |
| WO | 2013/008300 A1 | 1/2013 |
| WO | 2016/013090 A1 | 1/2016 |
| WO | 2017/208529 A1 | 12/2017 |
| WO | 2017/209225 A1 | 12/2017 |
| WO | 2019/177002 A1 | 9/2019 |

OTHER PUBLICATIONS

International Search Report for PCT Application No. PCT/JP2019/047514, mailed on Feb. 10, 2020.

Nakai, Rena, "Imaging technology used in automobiles, Hight accuracy and low-cost driver and cabin monitoring realized by the latest deep learning", Eizojoho Industrial, Aug. 1, 2019, vol. 51. No. 4, pp. 21-23.

Wada, T. et al., "Analysis of driver's head tilt using a mathematical model of motion sickness", International Journal of Industrial Ergonomics, Jan. 2018, vol. 63, pp. 89-97, in particular, p. 96, left column lines 53-60, right column, lines 31-41 in particular, p. 96, left column, lines 53-60, right column, lines 31-41.

JP Office Action for JP Application No. 2024-087375, mailed on Jan. 21, 2025 with English Translation.

US Office Communication for U.S. Appl. No. 18/500,436, mailed on Mar. 13, 2025.

\* cited by examiner

\<AN EXAMPLE OF FEATURE VECTOR\>

| | |
|---|---|
| (1) | CORRELATION BETWEEN FACE POSITION AND RIGHT PUPIL POSITION |
| (2) | CORRELATION BETWEEN FACE POSITION AND LEFT PUPIL POSITION |
| (3) | CORRELATION BETWEEN FACE PAN DIRECTION AND GAZE HORIZONTAL DIRECTION |
| (4) | CORRELATION BETWEEN FACE TILT DIRECTION AND GAZE VERTICAL DIRECTION |
| (5) | RATIO IN MOVING VELOCITY BETWEEN FACE GRAVITY-CENTER POSITION AND RIGHT EYE POSITION |
| (6) | RATIO IN MOVING VELOCITY BETWEEN FACE GRAVITY-CENTER POSITION AND LEFT EYE POSITION |
| (7) | RATIO IN ANGULAR VELOCITY BETWEEN FACE PAN DIRECTION AND GAZE HORIZONTAL DIRECTION |
| (8) | RATIO IN ANGULAR VELOCITY BETWEEN FACE TILT DIRECTION AND GAZE VERTICAL DIRECTION |

FIG. 5

ABNORMAL PHYSICAL CONDITION DETERMINATION SYSTEM, ABNORMAL PHYSICAL CONDITION DETERMINATION METHOD, AND COMPUTER PROGRAM

This application is a National Stage Entry of PCT/JP2019/047514 filed on Dec. 4, 2019, the contents of all of which are incorporated herein by reference, in their entirety.

TECHNICAL FIELD

The present invention relates to an abnormal physical condition determination system, an abnormal physical condition determination method, and a computer program that determine an abnormal physical condition of a target person.

BACKGROUND ART

A known system of this type determines a condition of a target person on the basis of an image obtained by imaging the target person. For example, Patent Literature 1 discloses a technique/technology of estimating a condition of a driver from a position of a face, a direction of the face, a gaze direction, and the like that are obtained by analyzing a face image. Patent Literature 2 discloses a technique/technology of detecting a face position from a face image and estimating the condition of the driver by using a degree of opening and closing of an eye, the gaze direction, the direction of the face, and the like.

As another related art, for example, Patent Literature 3 discloses a technique/technology of detecting a feature point vector from a plurality of feature points extracted from image data on a face.

CITATION LIST

Patent Literature

Patent Literature 1: International Publication No. WO2017/209225
Patent Literature 2: International Publication No. WO2017/208529
Patent Literature 3: International Publication No. WO2016/013090

SUMMARY

Technical Problem

When an attempt is made to determine the condition of the target person by directly utilizing a feature, such as the position of the face, the direction of the face, and the gaze direction, it is assumed that the condition will be affected by environmental variations such as, for example, individual differences and lighting conditions. In this case, depending on an environment when the condition is determined, there is a possibility that the accuracy of the determination is reduced. In other words, in the techniques/technologies as described in Patent Literatures 1 2 and 3, the condition of the target person cannot be accurately determined depending on the circumstances, which is technically problematic.

The present invention has been made in view of the above problems, and it is an example object of the present invention is to provide an abnormal physical condition determination system, an abnormal physical condition determination method, and a computer program that are appropriately determine an abnormal physical condition of a target person.

Solution to Problem

An abnormal physical condition determination system according to an example aspect of the present invention includes: an extraction unit that extracts a plurality of feature quantities indicating a condition of a target person from an image of the target person; an accumulation unit that accumulates the plurality of feature quantities as time series data; a calculation unit that calculates a relationship between each feature quantity from the plurality of feature quantities accumulated in the accumulation unit; and a determination unit that determines an abnormal physical condition of the target person on the basis of the relationship.

An abnormal physical condition determination method according to an example aspect of the present invention includes: extracting a plurality of feature quantities indicating a condition of a target person from an image of the target person; accumulating the plurality of feature quantities as time series data; calculating a relationship between each feature quantity from the plurality of feature quantities accumulated in the accumulation unit; and determining an abnormal physical condition of the target person on the basis of the relationship.

A computer program of the present invention operates a computer: to extract a plurality of feature quantities indicating a condition of a target person from an image of the target person; to accumulate the plurality of feature quantities as time series data; to calculate a relationship between each feature quantity from the plurality of feature quantities accumulated in the accumulation unit; and to determine an abnormal physical condition of the target person on the basis of the relationship.

Effect of the Invention

According to the abnormal physical condition determination system, the abnormal physical condition determination method, and the computer program in the respective aspects described above, it is possible to appropriately determine the abnormal condition of the target person.

BRIEF DESCRIPTION OF DRAWINGS

FIG. 5 is a table illustrating a specific example of a feature vector.

DESCRIPTION OF EXAMPLE EMBODIMENTS

Hereinafter, example embodiments of an abnormal physical condition determination system, an abnormal physical condition determination method, and a computer program will be described with reference to the drawings.

First Example Embodiment

An abnormal physical condition determination system according to a first example embodiment will be described with reference to FIG. 1 to FIG. 5. In the following, a description will be made to an example in which the abnormal physical condition determination system is an apparatus that determines an abnormal physical condition of an occupant of a vehicle (specifically, a motion sickness). (System Configuration)

Figure 1:
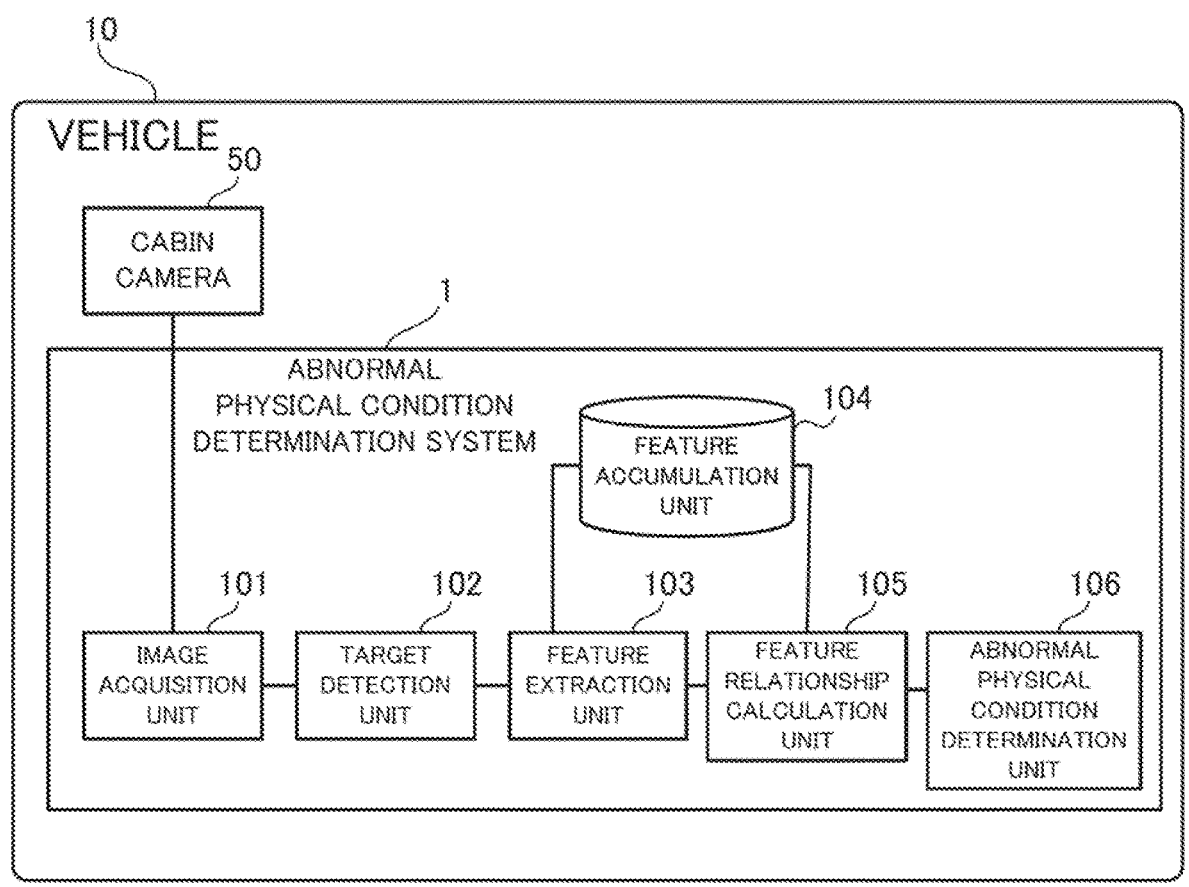
FIG. 1 is a block diagram illustrating an overall configuration of an abnormal physical condition determination system according to a first example embodiment.
Figure 2:
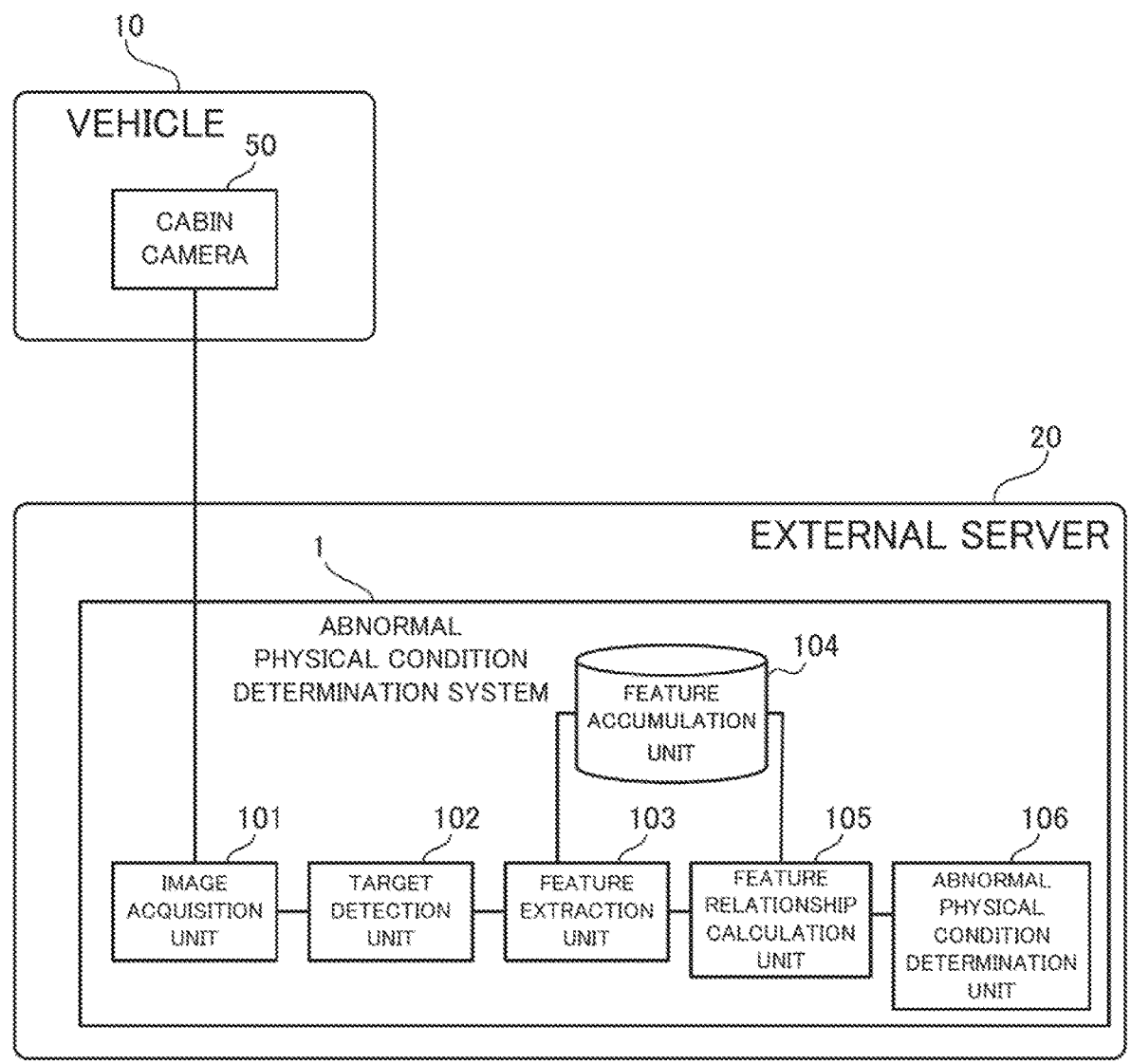
FIG. 2 is a block diagram illustrating an overall configuration of an abnormal physical condition determination system according to a modified example.

First, an overall configuration of the abnormal physical condition determination system according to the first example embodiment will be described with reference to FIG. 1 and FIG. 2. FIG. 1 is a block diagram illustrating the overall configuration of the abnormal physical condition determination system according to a first example embodiment. FIG. 2 is a block diagram illustrating an overall configuration of an abnormal physical condition determination system according to a modified example.

As illustrated in FIG. 1, an abnormal physical condition determination system 1 according to the first example embodiment is installed in a vehicle 10 including a cabin camera 50. The abnormal physical condition determination system 1 includes, as functional blocks for realizing its functions, an image acquisition unit 101, a target detection unit 102, a feature extraction unit 103, a feature accumulation unit 104, a feature relationship calculation unit 105, and an abnormal physical condition determination unit 106.

The image acquisition unit 101 is configured to obtain an image captured by the cabin camera 50 (specifically, an image of an occupant of the vehicle 10). The image obtained by the image acquisition unit 101 is configured to be outputted to the target detection unit 102.

The target detection unit 102 is configured to detect a target person whose abnormal physical condition is determined, from the image obtained by the image acquisition unit 101. The target detection unit 102 detects, for example, an area in which the target person appears, (e.g., a face area of the target person, etc.) from the captured image. Incidentally, as the existing techniques/technologies can be adopted as appropriate, a detailed description of a specific method of detecting the target person from the captured image will be omitted here. A detection result of the target detection unit 102 is configured to be outputted to the feature extraction unit 103.

The feature extraction unit 103 is configured to extract feature quantities for determining the abnormal physical condition of the target person from the area detected by the target detection unit 102. The feature quantities extracted by the feature extraction unit 103 include, for example, feature quantities related to the position of a pupil of the occupant, the direction of a face, a gaze direction, the color of the face, the position of a face feature point, and a degree of opening of a lid. The feature extraction unit 103 extracts a plurality of types of feature quantities from the occupant. The feature quantities extracted by the feature extraction unit 103 are configured to be outputted to each of the feature accumulation unit 104 and the feature relationship calculation unit 105.

The feature accumulation unit 104 is configured to accumulate the feature quantities extracted by the feature extraction unit 103, as time series data. The feature accumulation unit 104 accumulates the feature quantities, for example, in units of frames arranged in time series. The feature quantities accumulated in the feature accumulation unit 104 are configured to be appropriately outputted to the feature relationship calculation unit 105.

The feature relationship calculation unit 105 is configured to calculate a relationship between each feature quantity (i.e., a relationship between different types of feature quantities), from time series data on a plurality of types of feature quantities. More specifically, the feature relationship calculation unit 105 calculates the relationship between each feature quantity, from the feature quantities extracted by the feature extraction unit 103 (in other words, current feature quantities) and the feature quantities read from the feature accumulation unit 104 (in other words, past feature quantities). The relationship between each feature quantity is calculated, for example, as a feature vector having a plurality of dimensions. The relationship between each feature quantity calculated by the feature relationship calculation unit 105 is configured to be outputted to the abnormal physical condition determination unit 106.

The abnormal physical condition determination unit 106 determines the abnormal physical condition of the occupant on the basis of the relationship between each feature quantity calculated by the feature relationship calculation unit 105. The abnormal physical condition determination unit 106 determines, for example, whether or not the occupant is in an abnormal physical condition, or a degree of the abnormal physical condition of the occupant. Incidentally, the determination of the abnormal physical condition can be performed by setting a relevance between the abnormal physical condition and the relationship of feature quantities in advance. For example, a threshold for the feature vector may be set, and when the calculated feature vector exceeds the threshold, it may be determined that the occupant is in the abnormal physical condition. Furthermore, the abnormal physical condition determination unit 106 may be configured to learn the threshold associated with the determination. For example, the abnormal physical condition determination unit 106 may perform learning by using correct data or the like obtained by an input made by the occupant.

As illustrated in FIG. 2, the abnormal physical condition determination system 1 may be provided in an external server 20 that is outside the vehicle 10. That is, the abnormal physical condition determination system 1 may not necessarily be installed in the vehicle 10. Instead of all the components of the abnormal physical condition determination system 1, a part of the components of the abnormal physical condition determination system 1 may be provided in the external server 20.

(Hardware Configuration)

Figure 3:
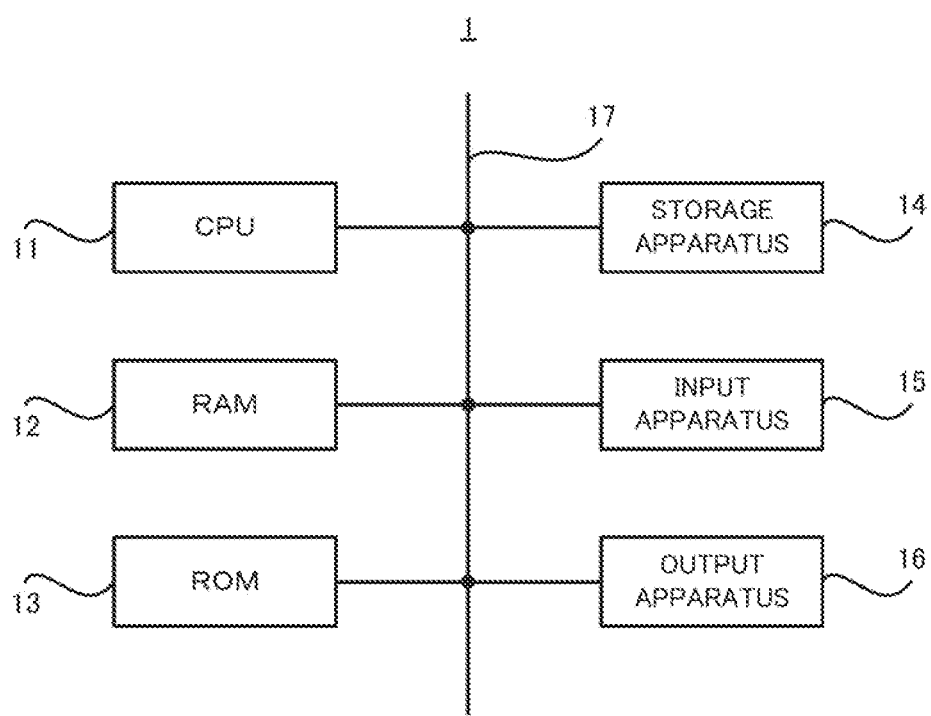
FIG. 3 is a block diagram illustrating a hardware configuration of the abnormal physical condition determination system according to the first example embodiment.

Next, a hardware configuration of the abnormal physical condition determination system 1 according to the first example embodiment will be described with reference to FIG. 3. FIG. 3 is a block diagram illustrating the hardware configuration of the abnormal physical condition determination system according to the first example embodiment.

As illustrated in FIG. 3, the abnormal physical condition determination system 1 according to the first example embodiment includes a CPU (Central Processing Unit) 11, a RAM (Random Access Memory) 12, a ROM (Read Only Memory) 13, and a storage apparatus 14. The abnormal physical condition determination system 1 may further include an input apparatus 15 and an output apparatus 16. The CPU 11, the RAM 12, the ROM 13, the storage apparatus 14, the input apparatus 15, and the output apparatus 16 are connected through a data bus 17.

The CPU 11 reads a computer program. For example, the CPU 11 is configured to read a computer program stored by at least one of the RAM 12, the ROM 13 and the storage apparatus 14. Alternatively, the CPU 11 may read a computer program stored by a computer readable recording medium by using a not-illustrated recording medium reading apparatus. The CPU 11 may obtain (i.e., read) a computer program from a not-illustrated apparatus that is located outside the physical condition determination system 1 through a network interface. The CPU 11 controls the RAM 12, the storage apparatus 14, the input apparatus 15, and the output apparatus 16 by executing the read computer program. Especially in the example embodiment, when the CPU 11 executes the computer program read by the CPU 11, a functional block for determining the abnormal physical condition is implemented in the CPU 11.

The RAM 12 temporarily stores the computer program to be executed by the CPU 11. The RAM 12 temporarily stores the data that is temporarily used by the CPU 11 when the CPU 11 executes the computer program. The RAM 12 may be, for example, a D-RAM (Dynamic RAM).

The ROM 13 stores the computer program to be executed by the CPU 11. The ROM 13 may otherwise store fixed data. The ROM 13 may be, for example, a P-ROM (Programmable ROM).

The storage apparatus 14 stores the data that is stored for a long term by the abnormal physical condition determination system 1. The storage apparatus 14 may operate as a temporary storage apparatus of the CPU 11. The storage apparatus 14 may include, for example, at least one of a hard disk apparatus, a magneto-optical disk apparatus, an SSD (Solid State Drive), and a disk array apparatus.

The input apparatus 15 is an apparatus that receives an input instruction from a user of the abnormal physical condition determination system 1. The input apparatus 15 may include, for example, at least one of a keyboard, a mouse, and a touch panel.

The output apparatus 16 is an apparatus that outputs information about the abnormal physical condition determination system 1 to the outside. For example, the output apparatus 16 may be a display apparatus (e.g., a display) that is configured to display the information about the abnormal physical condition determination system 1.

(Flow of Operation)

Figure 4:
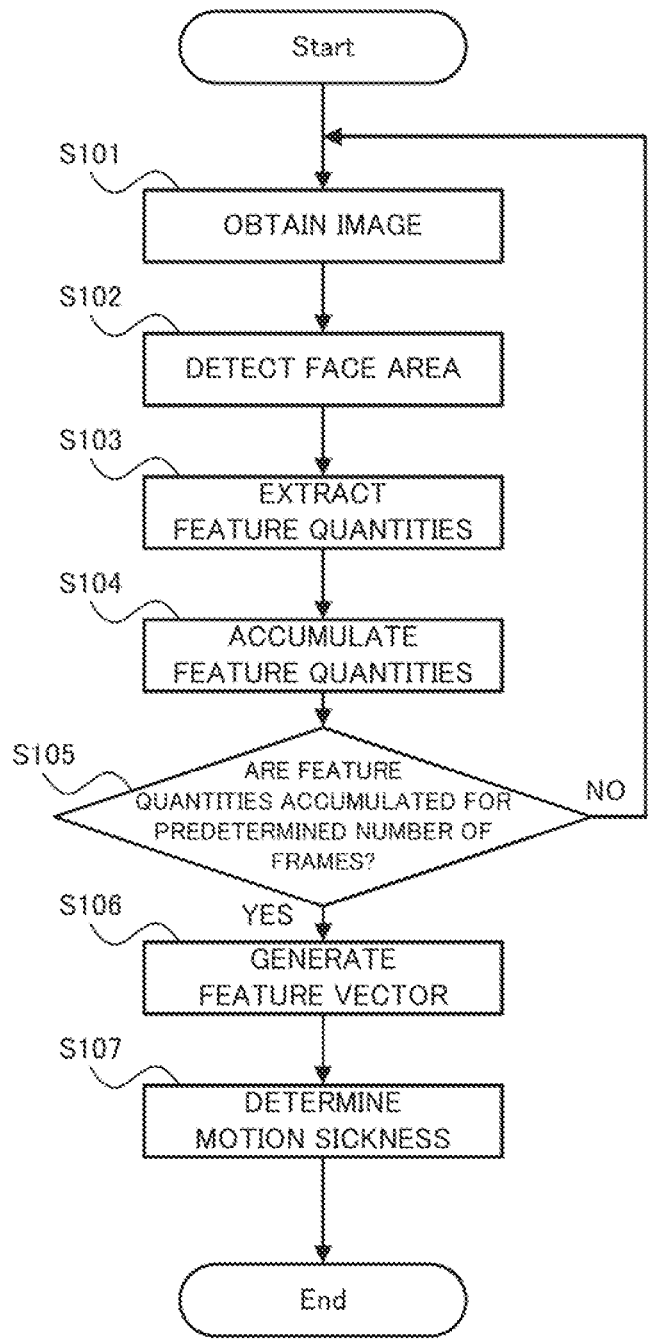
FIG. 4 is a flowchart illustrating a flow of operation of the abnormal physical condition determination system according to the first example embodiment.

Next, with reference to FIG. 4, a flow of operation of the abnormal physical condition determination system 1 according to the first example embodiment will be described. FIG. 4 is a flowchart illustrating the flow of the operation of the abnormal physical condition determination system according to the first example embodiment.

As illustrated in FIG. 4, in operation of the abnormal physical condition determination system 1 according to the first example embodiment, first, the image acquisition unit 101 obtains the image of the occupant captured by the cabin camera 50 (step S101). Then, the target detection unit 102 detects the face area from the image of the occupant (step S102). When the feature quantities are detected from other than the face area, another area corresponding to the feature quantities may be detected.

Then, the feature extraction unit 103 extracts the feature quantities from the face area (step S103). Then, the feature accumulation unit 104 accumulates (i.e., stores) the extracted feature quantities (step S104).

Then, the feature relationship calculation unit 105 determines whether or not the feature quantities are accumulated for a predetermined number of frames in the feature accumulation unit 104 (step S105). Here, the "predetermined number of frames" is a value corresponding to an amount of feature quantities sufficient to calculate the relationship between each feature quantity, and an optimum value (e.g., the number of frames corresponding to 5 seconds) is set in advance. When it is determined that the feature quantities are not accumulated for a predetermined number of frames (the step S105: NO), the process is performed from the step S101 again. That is, the process of extracting the feature quantities from the image of the occupant and accumulating them is repeated.

On the other hand, when it is determined that the feature quantities are accumulated for a predetermined number of frames (the step S105: YES), the feature relationship calculation unit 105 calculates the relationship between each feature quantity (step S106). Then, the abnormal physical condition determination unit 106 determines the abnormal physical condition of the occupant (here, a motion sickness) on the basis of the calculated relationship between each feature quantity (step S107).

Incidentally, a series of process steps described above is performed while the vehicle 10 is running. The abnormal physical condition determination system 1 may start the operation, for example, when the vehicle 10 starts to run. Furthermore, it may start the operation at a timing after a lapse of a predetermined time (a time in which the abnormality supposedly begins to appear in the physical condition of the occupant) from the start of the running. Here, the predetermined time may be arbitrarily set. Alternatively, the predetermined time may be set on the basis of a history information, wherein a time from the start of the running until the abnormality begins to appear in the physical condition of the occupant is stored as the history information. In this way, it is possible to reduce an unnecessary process in a period in which the occupant is not in an abnormal physical condition. Alternatively, the abnormal physical condition determination system 1 may start the operation at a timing at which the face of the occupant can be normally detected or at a timing at which the occupant gets in the vehicle. In this way, the face of the occupant can be tracked, and it is thus possible to prevent a situation in which the face of the occupant cannot be detected even though the occupant is in the abnormal physical condition. Alternatively, the abnormal physical condition determination system 1 may start the operation on the basis of a behavior information about the vehicle (e.g., at a timing at which a threshold of an acceleration sensor becomes greater than or equal to a predetermined threshold). In this way, it is possible to reduce an unnecessary process when the vehicle takes a behavior that hardly causes the abnormal physical condition.

Furthermore, the abnormal physical condition determination system 1 ends the operation, for example, at a timing when the vehicle 10 stops running. Alternatively, it may end the operation on the basis of the behavior information about the vehicle (e.g., at a timing at which the threshold of the acceleration sensor is less than or equal to a predetermined threshold).

(Specific Examples of Feature Vector)

Next, with reference to FIG. 5, the feature vector (i.e., the relationship between each feature quantity generated in the step S106 in FIG. 4) used in the abnormal physical condition determination system 1 according to the first example embodiment will be specifically described. FIG. 5 is a table illustrating a specific example of the feature vector.

In FIG. 5, it is assumed that the feature extraction unit 103 extracts positions of the occupant's right and left eye pupils, a face direction angle (pan, tilt, and roll directions), and a gaze angle (horizontal and vertical directions) as the feature quantities. In this case, the feature relationship calculation unit 105 calculates the relationship between the above-described plurality of types of feature quantities, as a multi-dimensional feature vector.

Specifically, the feature relationship calculation unit 105 calculates an eight-dimensional feature vector including (1) a correlation between a face position and a right pupil position, (2) a correlation between the face position and a left pupil position, (3) a correlation between a face pan direction and a gaze horizontal direction, (4) a correlation between a face tilt direction and a gaze vertical direction, (5) a ratio in a moving velocity between a face gravity-center position and a right eye position, (6) a ratio in the moving velocity between the face gravity-center position and a left eye position, (7) a ratio in an angular velocity between the face pan direction and the gaze horizontal direction, and (8) a ratio in the angular velocity between the face tilt direction and the gaze vertical direction. Taking (1) as an example, the correlation is obtained by dividing the covariance of the face position and the right pupil by the product of a standard deviation of the face position and a standard deviation of the right pupil.

Incidentally, for each element of the feature vector may be appropriately weighted. The weight in this case may be determined in accordance with a face condition estimated from the image of the face area. Specifically, when the occupant wears glasses, the weight of the feature quantity related to the eyes may be reduced because the accuracy of the feature quantity obtained for the eyes is considered to be reduced. Furthermore, the feature vector does not need to be eight-dimensional, and may have dimensionality that is appropriately set.

The abnormal physical condition determination unit 106 determines that the occupant is in the abnormal physical condition on the basis of the calculated relationship between each feature quantity. Specifically, when the correlation and the ratio calculated by the feature relationship calculation unit 105 are greater than or equal to a predetermined value, it is determined that the occupant is in the abnormal physical condition. Incidentally, in calculating the eight-dimensional feature vector including the above-described (1) to (8), it may be determined that the occupant is in the abnormal physical condition when any one or more correlations or ratios are greater than or equal to a predetermined value, or it may be determined that the occupant is in the abnormal physical condition when all the eight correlations and ratios are greater than or equal to respective predetermined values.

When having a motion sickness, the occupant feels vertigo, or dizziness in eye opening. On the other hand, the above-described (1) to (8) in the feature vector are calculated as the relationship between a pair of feature quantities that normally changes in the same manner. Therefore, according to the feature vector described above, it is possible to discriminate a situation in which the movements of the face and eyes do not correspond to each other due to dizziness, and it is possible to suitably determine the occurrence of the motion sickness.

Incidentally, the feature vector described above is merely an example, and another relationship of feature quantities may be used. For example, a pair of feature quantities for calculating their relationship may be determined in accordance with the type of the abnormal physical condition that is to be determined.

(Technical Effect)

Next, a technical effect obtained by the abnormal physical condition determination system 1 according to the first example embodiment will be described.

As described in FIG. 1 to FIG. 5, according to the abnormal physical condition determination system 1 in the first example embodiment, it is possible to determine the motion sickness of the occupant on the basis of the feature quantities extracted from the image of the occupant. Especially in this example embodiment, the motion sickness is determined on the basis of the relationship between a plurality of feature quantities, rather than by directly utilizing the extracted feature quantities. Therefore, for example, it is possible to suppress an influence of environmental variations, such as individual differences and lighting conditions, and it is possible to determine the motion sickness with high accuracy. In addition, since the feature quantities that are time series data are utilized, unlike the case where the feature quantities are extracted from only one image, a change per unit time in the feature quantities can also be considered. Therefore, it is possible to determine the motion sickness, more accurately.

The above example embodiment describes an example of determining the motion sickness of the occupant of the vehicle 10, but the motion sickness of the occupant of a movable body other than the vehicle 10, such as, for example, a ship or an airplane, may be also determined. In addition, an abnormal physical condition other than the motion sickness may be determined. Specifically, a determination may be performed on dizziness that may occur in the use of a VR (Virtual Reality) apparatus (so-called VR sickness) or the like. If the feature quantity related to the face of the target person is utilized as in the example embodiment, it is possible to appropriately determine the abnormal physical condition that is especially accompanied by dizziness, but it can also be applied to the determination of another abnormal physical condition that is not accompanied by dizziness, by utilizing the relationship between appropriate feature quantities.

Second Example Embodiment

Next, the abnormal physical condition determination system 1 according to a second example embodiment will be described with reference to FIG. 6 to FIG. 12. The second example embodiment is partially different from the above-described first example embodiment only in the configuration and operation, and is substantially the same in the other parts. Therefore, the parts that differ from the first example embodiment will be described in detail below, and the other overlapping parts will be omitted as appropriate.

(System Configuration)

Figure 6:
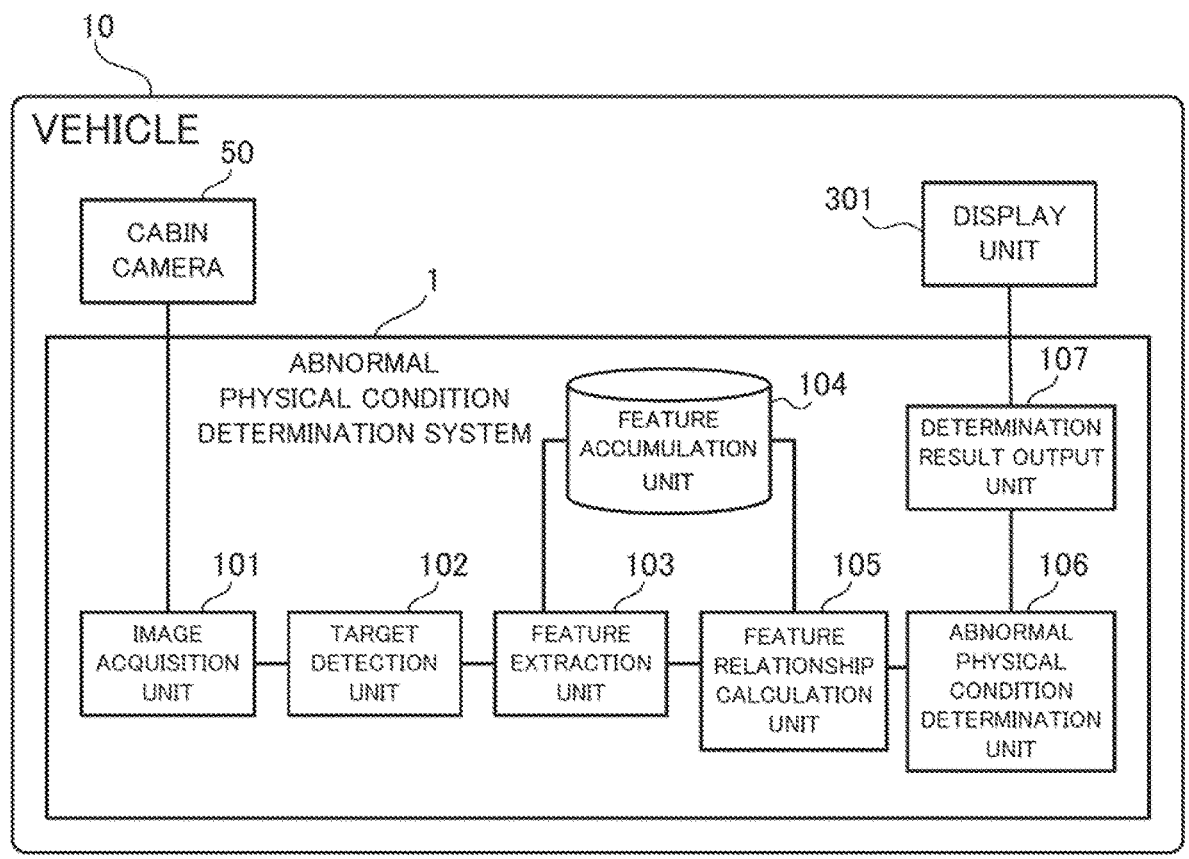
FIG. 6 is a block diagram illustrating an overall configuration of an abnormal physical condition determination system according to a second example embodiment.
Figure 7:
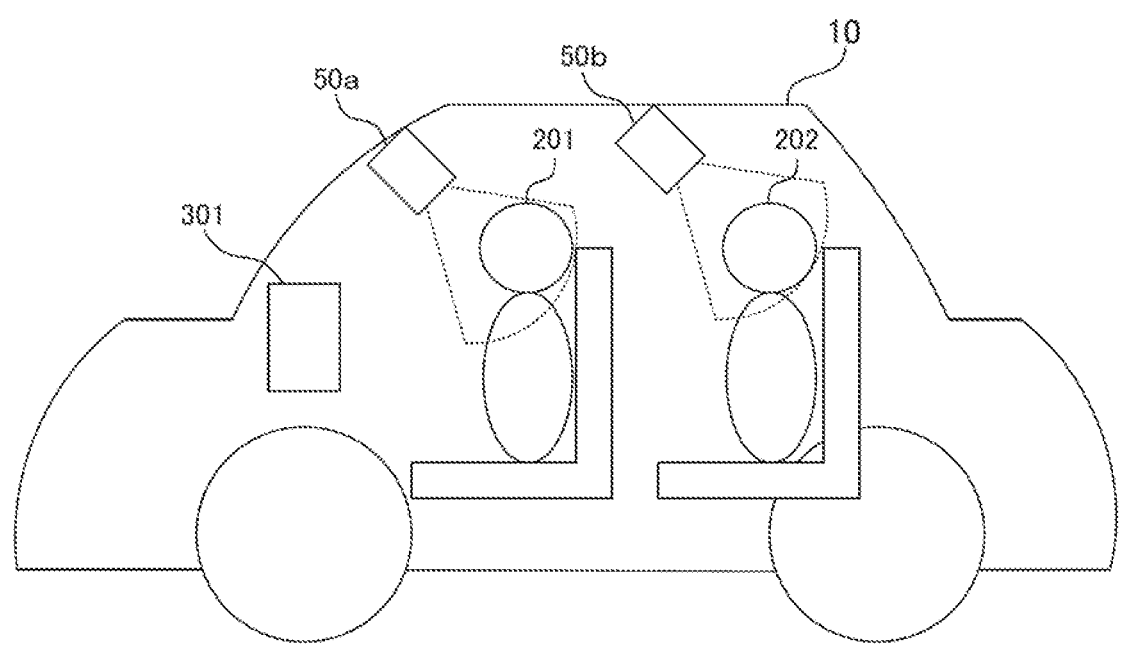
FIG. 7 is a schematic diagram illustrating an interior configuration of a vehicle to which the abnormal physical condition determination system according to the second example embodiment is applied.

First, an overall configuration of the abnormal physical condition determination system 1 according to the second example embodiment will be described with reference to FIG. 6 and FIG. 7. FIG. 6 is a block diagram illustrating the overall configuration of the abnormal physical condition determination system according to the second example embodiment. FIG. 7 is a schematic diagram illustrating an interior configuration of a vehicle to which the abnormal physical condition determination system according to the second example embodiment is applied. Incidentally, in FIG. 6, the same components as those illustrated in FIG. 1 carry the same reference numerals.

As illustrated in FIG. 6, the abnormal physical condition determination system 1 according to the second example embodiment includes a determination result output unit 107 in addition to the components of the abnormal physical condition determination system 1 according to the first example embodiment (see FIG. 1).

The abnormal physical condition determination unit 106 may identify a cause of the abnormal physical condition of the occupant from the information indicating the behavior of the vehicle 10. In this case, the abnormal physical condition determination unit 106 may be configured to obtain the information indicating the behavior of the vehicle 10 from a not-illustrated sensor (e.g., an acceleration sensor or the like) provided in the vehicle 10. Furthermore, the abnormal physical condition determination unit 106 may identify the cause of the abnormal physical condition of the occupant from an analysis result of the image of the occupant, or the like. In this case, the abnormal physical condition determination unit 106 may be configured to extract the feature quantity that allows the cause of the abnormal physical condition to be determined, from an image or the like including a whole body of the occupant. In addition, a not-illustrated abnormal physical condition cause identification unit may identify the cause of the abnormal physical condition of the occupant.

For example, when it is determined that the occupant is in the abnormal physical condition, the abnormal physical condition determination unit 106 obtains an acceleration of the vehicle at the determined timing. The abnormal physical condition determination unit 106 compares the obtained acceleration with a threshold stored in advance (e.g., an acceleration that likely causes the abnormal physical condition), thereby to determine whether or not the abnormal physical condition of the occupant is due to the acceleration of the vehicle 10. The obtained acceleration may be an acceleration at a timing a predetermined period before the timing at which it is determined that the occupant is in the abnormal physical condition. Alternatively, it may be an acceleration in a predetermined period until the timing at which it is determined that the occupant is in the abnormal physical condition. Furthermore, in place of or in addition to the acceleration, at least one of a velocity, an angular velocity, an angular velocity in a yaw direction, an angular acceleration in the yaw direction, an angular velocity in a pitch direction, an angular acceleration in the pitch direction, an angular velocity in a roll direction, and an angular acceleration in the roll direction may be obtained. The cause may be identified on the basis of at least one of them or all of them.

Incidentally, the abnormal physical condition determination unit 106 may identify the cause of the abnormal physical condition without comparing the detected acceleration or the like with the threshold. For example, with respect to the acceleration detected at the timing at which it is determined that the occupant is in the abnormal physical condition, it can be determined that the acceleration itself is the cause of the abnormal physical condition. Therefore, the acceleration detected at the timing at which it is determined that the occupant is in the abnormal physical condition or the like may be identified as the cause of abnormal physical condition as it is.

Furthermore, for example, when it is determined that the occupant is in the abnormal physical condition, the abnormal physical condition determination unit 106 specifies what action (e.g., reading, eating and drinking, etc.) the occupant is taking, from a camera image at the determined timing. The abnormal physical condition determination unit 106 determines whether or not the abnormal physical condition of the occupant is due to the action of the occupant, from whether or not the specified action corresponds to the cause of the abnormal physical condition stored in advance (e.g., a table information about the action that likely causes the abnormal physical condition). Incidentally, the camera image used to identify the cause may be captured or photographed at a timing a predetermined period before the timing at which it is determined that the occupant is in the abnormal physical condition. Alternatively, it may be captured in a predetermined period until the timing at which it is determined that the occupant is in the abnormal physical condition. In addition, the table information about the action that likely causes the abnormal physical condition may be associated with the degree of the abnormal physical condition for each action. Alternatively, multiple actions may be obtained, and the cause may be identified on the basis of at least one of them or all of them.

The determination result output unit 107 is configured to output a determination result of the abnormal physical condition determination unit 106, to a display unit 301 mounted on the vehicle 10. That is, the determination result output unit 107 outputs information about the physical condition abnormal of the occupant, so as to present to the occupant or a fellow occupant. Incidentally, the determination result output unit 107 may be configured to output the information about the abnormal physical condition of the occupant, to a not-illustrated speaker or the like.

As illustrated in FIG. 7, the display unit 301 is configured as a display or the like provided on a front side of the vehicle. The cabin camera 50 is provided as a camera 50*a* that is configured to image the faces of occupants 201 in a driver's seat and a passenger seat, and a camera 50*b* that is configured to image the face of an occupant 202 in a rear seat.

(Example of Display by Display Unit)

Figure 8:
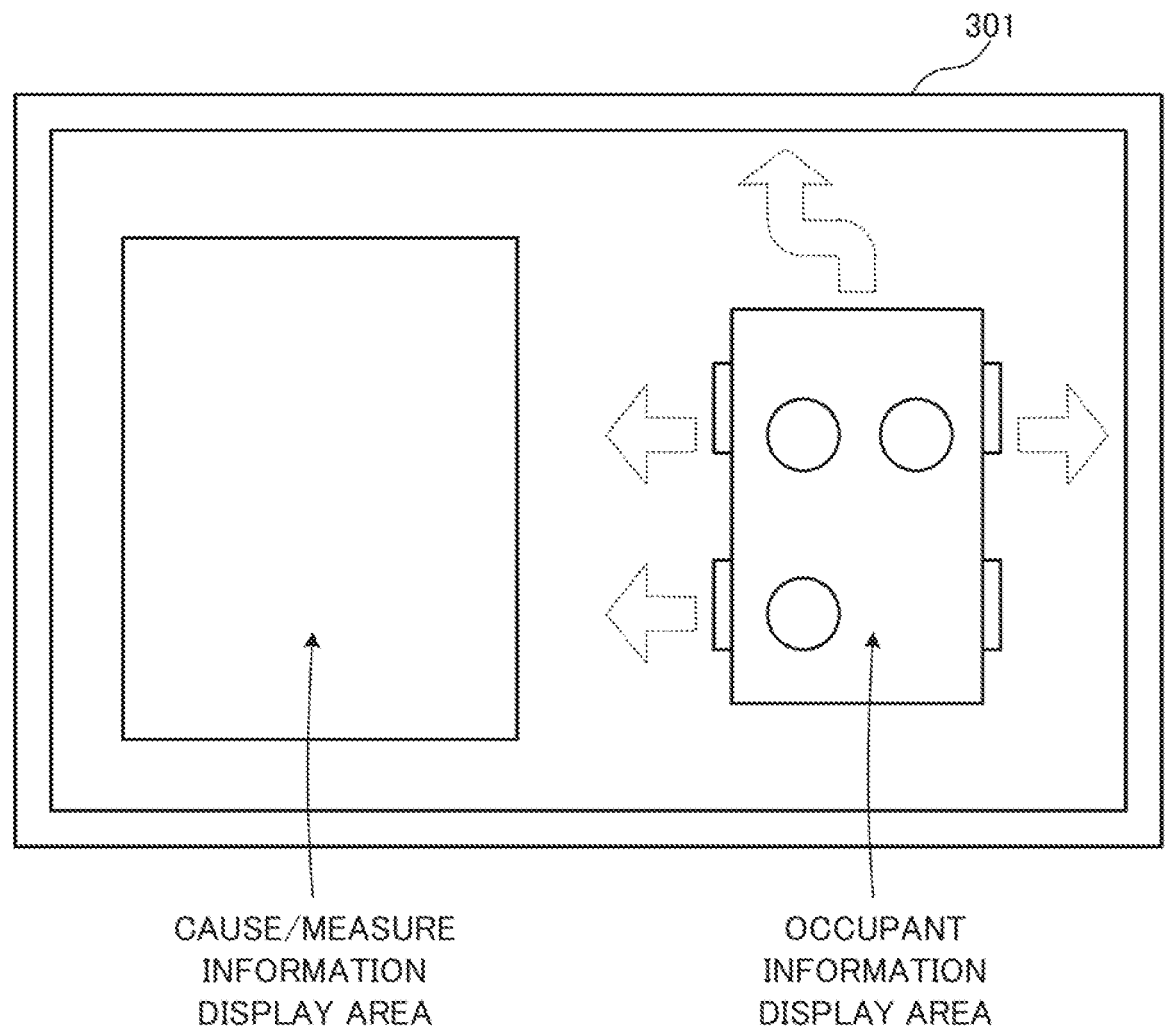
FIG. 8 is a diagram illustrating an example of a display area of a display unit.
Figure 9:
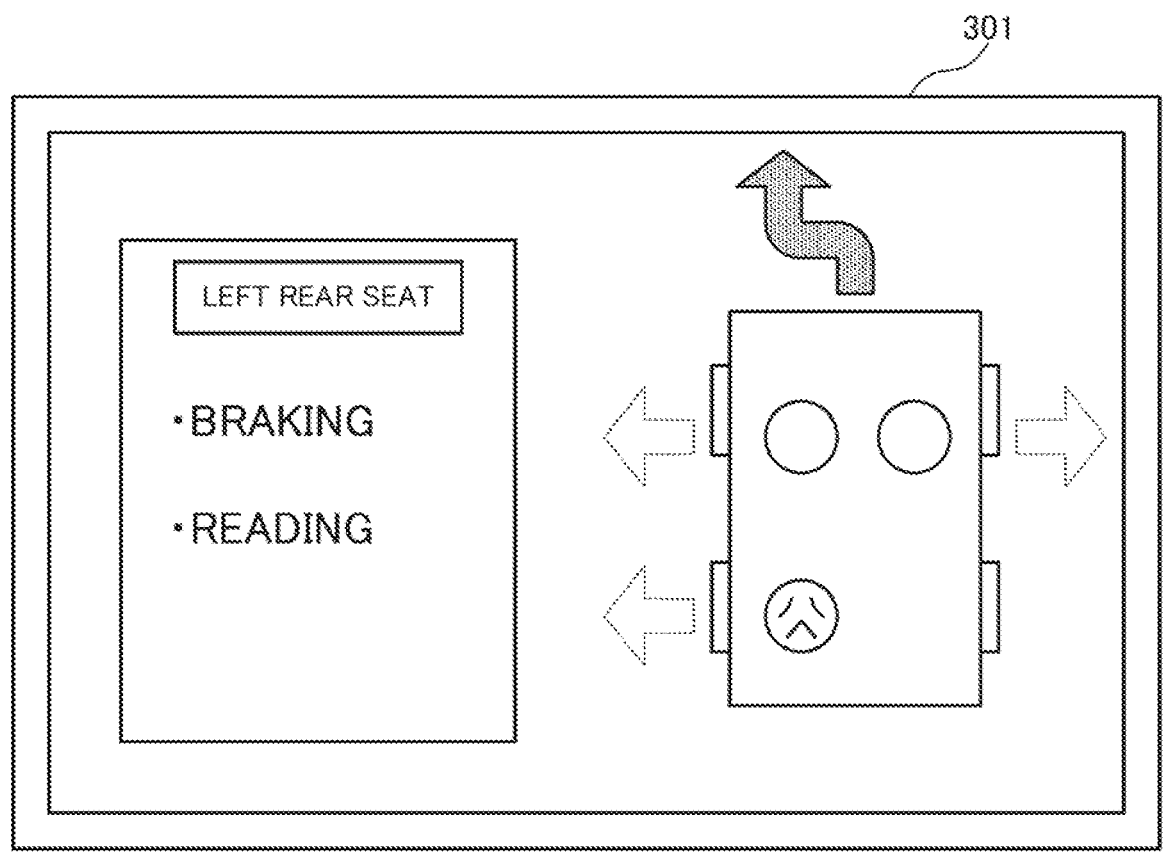
FIG. 9 is version 1 of a diagram illustrating a display example in the display area when an occupant has a car sickness.
Figure 10:
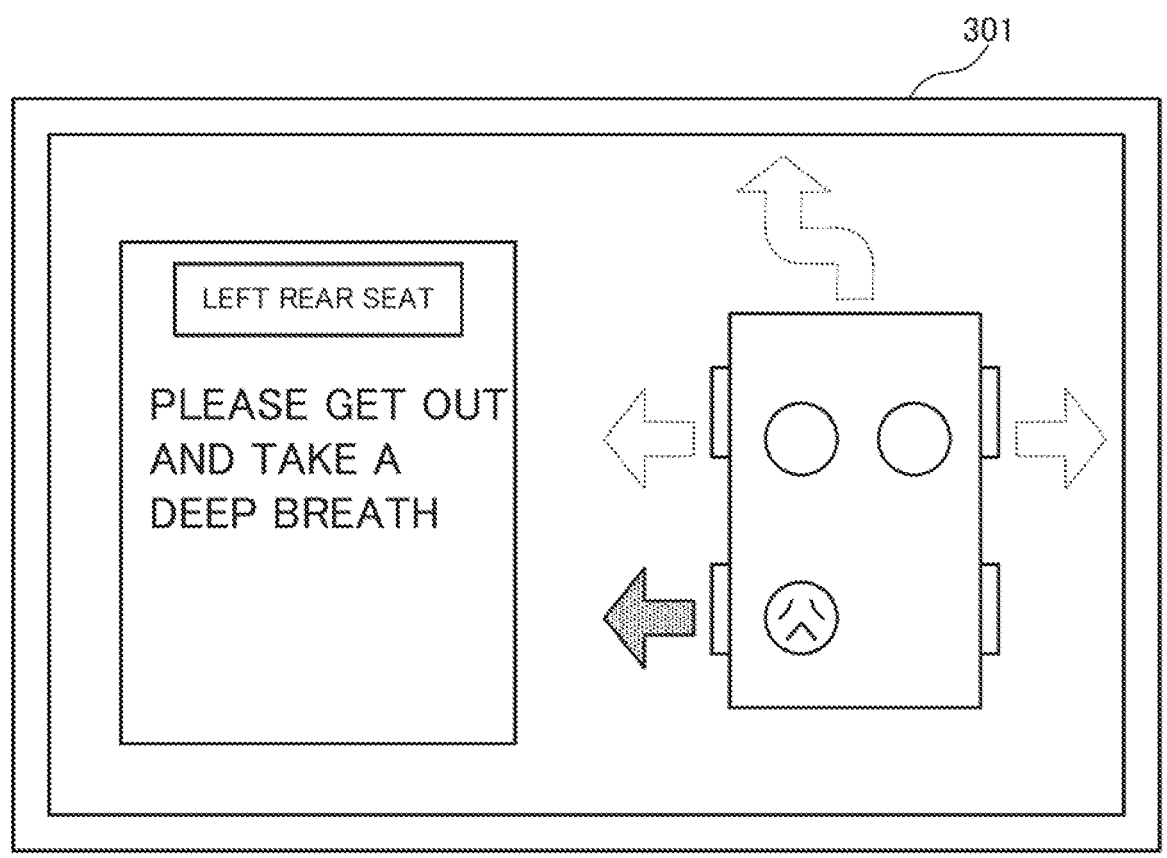
FIG. 10 is version 2 of a diagram illustrating a display in the display area when the occupant has a car sickness.
Figure 11:
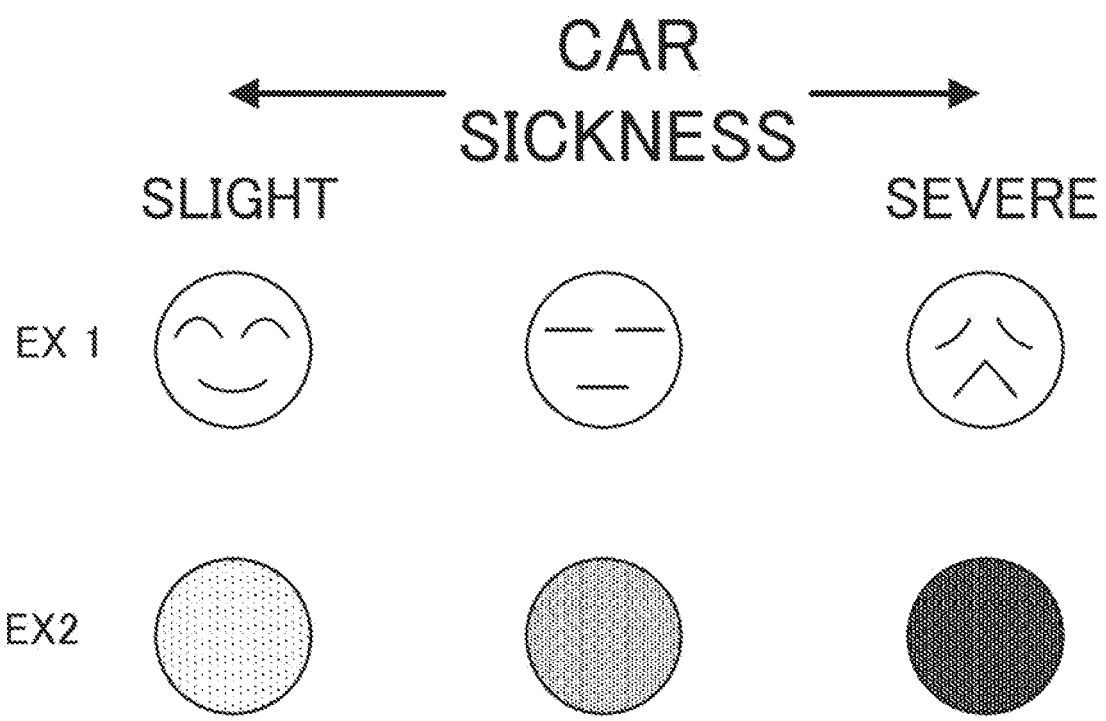
FIG. 11 is a diagram illustrating an example of an icon illustrating a degree of the car sickness.
Figure 12:
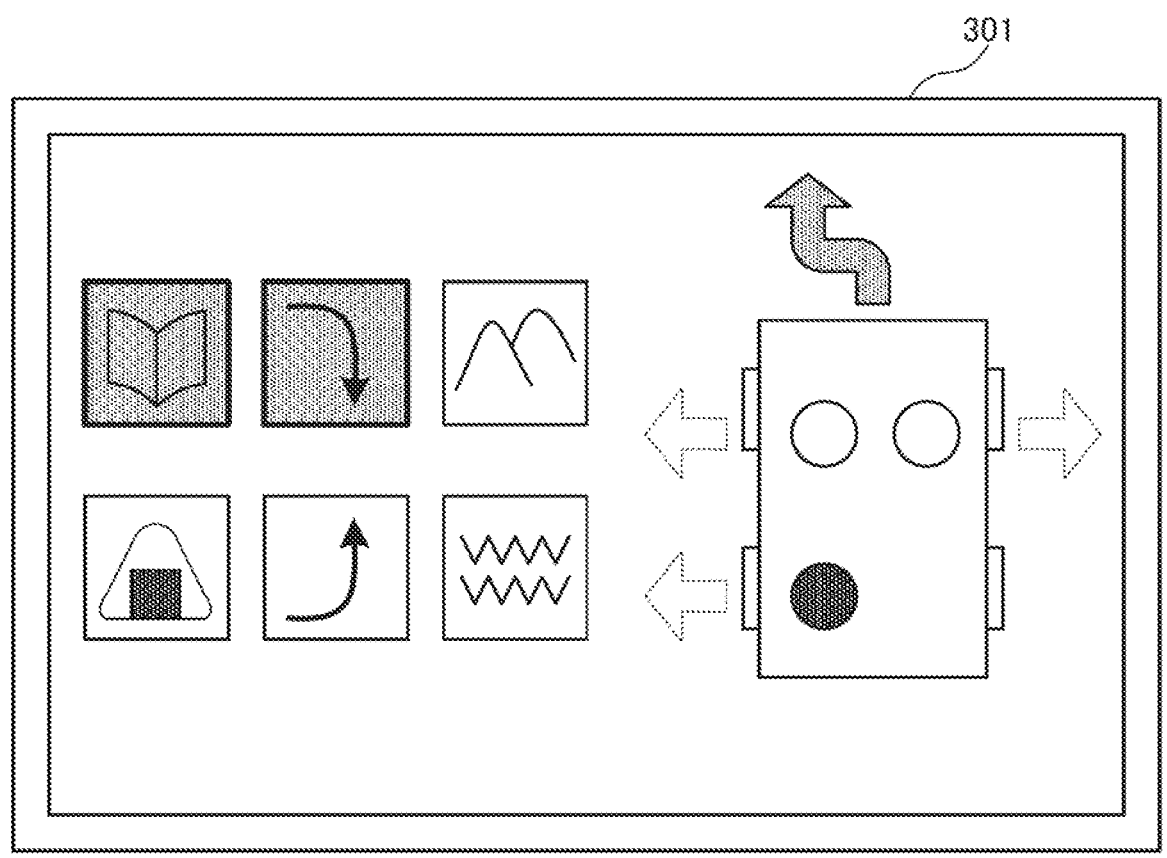
FIG. 12 is a diagram illustrating another display example in the display area of the display unit.

Next, a display example by the abnormal physical condition determination system 1 according to the second example embodiment (i.e., a specific display example of the display unit 301) will be described with reference to FIG. 8 to FIG. 12. FIG. 8 is a diagram illustrating an example of a display area of the display unit. FIG. 9 is version 1 of a diagram illustrating a display example in the display area when the occupant has a car sickness. FIG. 10 is version 2 of a diagram illustrating a display in the display area when the occupant has a car sickness. FIG. 11 is a diagram illustrating an example of an icon illustrating a degree of the car sickness. FIG. 12 is a diagram illustrating another display example in the display area of the display unit.

The display area of the display unit 301 may include a cause/measure information display area. The display area of the display unit 301 may also include an occupant information display area. An example is illustrated in FIG. 8. The cause/measure information display area located on a left side shows at least one of a cause and a measure in accordance with a determination result about the motion sickness. If there is no occupant who has a motion sickness, nothing may be displayed in the cause/measure information display area. The occupant information display area located on a right side shows information about the occupant of the vehicle 10 and information about instructions to the occupant. In this example, since there are a total of three occupants, which are one in the driver's seat, one in the passenger seat, and one in the left rear seat, an icon indicating the presence of the occupant (a circular icon in FIG. 8) is displayed in each seat.

In the example illustrated in FIG. 9, the occupant in the left rear seat is having a motion sickness. For this reason, the icon corresponding to the occupant in the left rear seat in the occupant information display area is changed to an icon indicating the motion sickness. In addition, an arrow icon (an icon in front of the vehicle) in the occupant information display area is turned on. This icon indicates that it recommends pulling over. In such cases, a driving route for pulling over or parking the vehicle 10 in a parking space may be displayed in conjunction with a navigation apparatus.

The cause/measure information display area shows the cause of the motion sickness of the occupant in the left rear seat (here, braking and reading). Incidentally, the cause of the motion sickness may be identified by the abnormal physical condition determination unit 106 or a not-illustrated abnormal physical condition cause specifying unit, as described above. When there is more than one occupant who is having a motion sickness, the cause/measure information display area may be divided in accordance with the number of the occupants and each division may perform a corresponding display. In addition, although it is not illustrated here, more specific instructions may be displayed as a measure against the abnormal physical condition, such as "Driver should be careful not to apply a brake" and "Person in the left rear seat should stop reading", on the basis of the identified cause of the abnormal physical condition.

Incidentally, the display of the cause and measure may use a template information prepared in advance. For the template information, contents of the cause such as "sudden braking" and "reading" and contents of instructions such as "the driver should drive carefully" and "the occupants should stop reading and drinking" may be set as at least one display information. The template information may be an icon image indicating the cause and measure. In addition, when the abnormal physical condition of the occupant is detected, the template information may be used without identifying the cause of the abnormal physical condition.

Alternatively, in addition to or in place of the display of the display unit 301, voice guidance may be provided.

The example illustrated in FIG. 10 is a display example obtained after the vehicle 10 is pulled over after the situation illustrated in FIG. 9 occurs. In the occupant information display area, the arrow icon that is turned on in FIG. 9 is turned off because the vehicle 10 is pulled over. On the other hand, an arrow icon near the occupant in the left rear seat is turned on. This arrow icon recommends the occupant in the left rear seat to get out of the vehicle 10.

The cause/measure information display area shows contents of an instruction that is "Please get out and take a deep breath". That is, a measure to reduce the motion sickness is displayed. Incidentally, the display example here is merely an example, and another measure may be displayed. For example, such a display that encourages the occupant to look out of the window, to adjust the seat to easily look outside, to move to the passenger seat, to take a motion sickness pill, or the like may be provided. Alternatively, a driving route suitable to take the measure may be displayed in conjunction with a navigation apparatus. Specifically, a choice of whether or not to the occupant needs a motion sickness pill may be displayed and the occupant's reply may be accepted (an inquiry may be made by audio and the occupant's reply may be accepted by voice recognition), and when the occupant replies that he or she needs it, a driving route to a nearby pharmacy may be displayed.

One of the causes of the motion sickness is that the occupant other than the driver cannot predict the behavior of the vehicle 10. As a measure for such a cause, when there is an occupant who has a motion sickness, a display or a voice guidance related to the behavior of the vehicle 10 may be provided. For example, on the basis of information about a driving road, in which direction and in how many seconds the vehicle 10 turns may be voice-guided. Alternatively, in which direction the vehicle 10 turns or in how many seconds the vehicle 10 moves may be displayed on the display unit 301.

As illustrated in FIG. 11, the icon of the occupant displayed in the occupant information display area varies depending on the degree of the motion sickness. For example, in Example 1, an expression of the icon varies depending on the degree of the motion sickness. In Example 2, brightness and color of the icon varies depending on the degree of the motion sickness. When changing the color of the icon, it is preferable to adopt a color from which emergency can be intuitively grasped. Specifically, it may be changed to "green" when the degree of the motion sickness is slight, to "yellow" when the degree of the motion sickness is moderate, and to "red" when the degree is severe. Although an example of changing the icon in three stages is illustrated here, the number of types of the icon may be increased or reduced in accordance with the degree, such as, for example, in five stages.

As illustrated in FIG. 12, the cause/measure information display area may be icon-displayed. The icons in FIG. 12 indicate the cause of the motion sickness. The icons in the upper row indicate "reading", "sudden braking", and "not looking outside" in order from the left. The icons in the lower row indicate "eating and drinking", "sudden start" and "vibration" in order from the left. In the example of FIG. 12, the icons of "reading" and "sudden braking" are turned on because they are estimated to be the cause of the motion sickness.

(Technical Effect)

Next, a technical effect obtained by the physical condition abnormality determination system 1 according to the second example embodiment will be described.

As described in FIG. 6 to FIG. 12, according to the abnormal physical condition determination system 1 in the second example embodiment, it is possible to accurately inform the occupant of the vehicle 10 of a current situation by displaying the determination result about the motion sickness. Furthermore, the display of the cause and measure of the motion sickness makes it easy to attempt to remove the motion sickness. As in the first example embodiment, the second example embodiment can be also applied to motion sickness that occurs in a movable body other than the vehicle 10 or the abnormal physical condition other than the motion sickness.

Third Example Embodiment

Next, the abnormal physical condition determination system 1 according to a third example embodiment will be described with reference to FIG. 13. The third example embodiment is partially different from the above-described first and second example embodiments only in the configuration and operation, and is substantially the same in the other parts. Therefore, the parts that differ from the first and second example embodiments will be described in detail below, and the other overlapping parts will be omitted as appropriate.

(System Configuration)

First, an overall configuration of the abnormal physical condition determination system 1 according to the third example embodiment will be described with reference to FIG. 13. FIG. 13 is a block diagram illustrating the overall configuration of the abnormal physical condition determination system according to the third example embodiment. Incidentally, in FIG. 13, the same components as those illustrated in FIG. 1 carry the same reference numerals.

Figure 13:
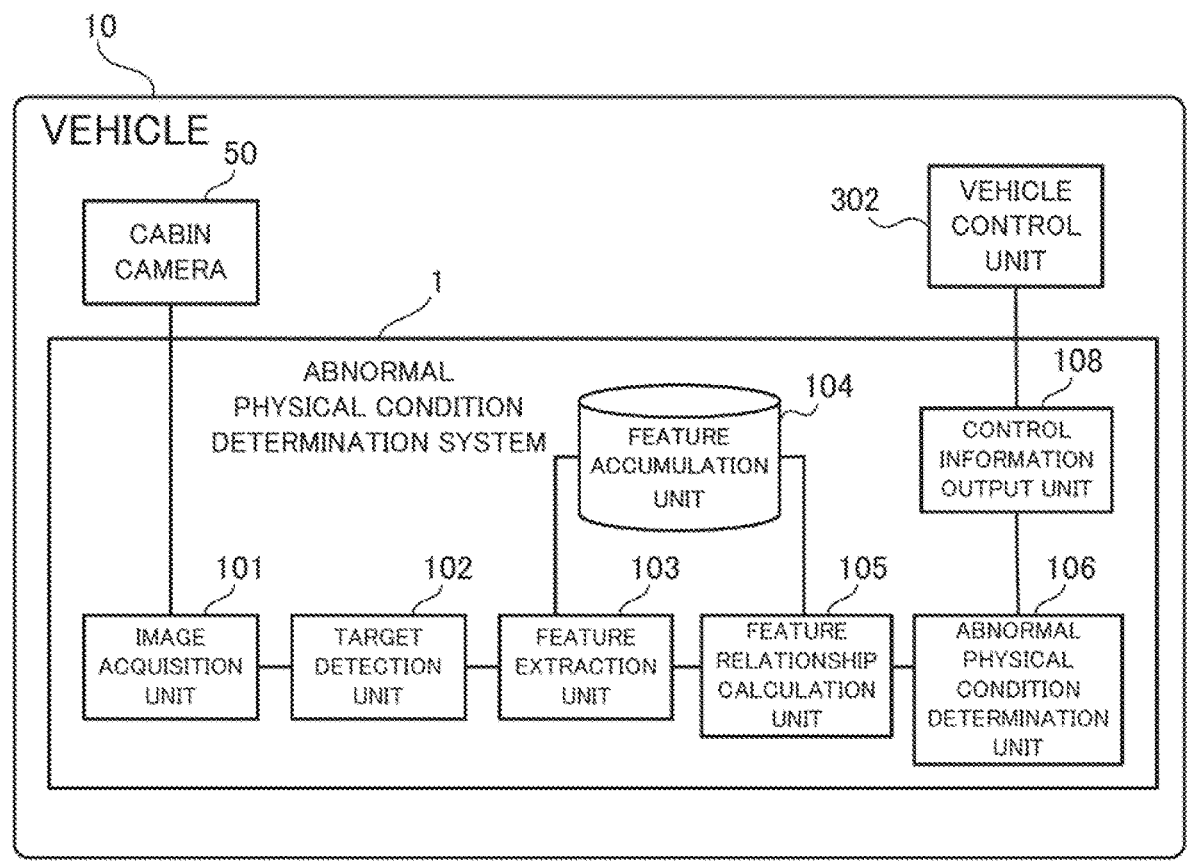
FIG. 13 is a block diagram illustrating an overall configuration of an abnormal physical condition determination system according to a third example embodiment.

As illustrated in FIG. 13, the abnormal physical condition determination system 1 according to the third example embodiment includes a control information output unit 108 in addition to the components of the abnormal physical condition determination system 1 according to the first example embodiment (see FIG. 1).

The control information output unit 108 generates and outputs a control information for controlling the vehicle 10 on the basis of the determination result about the abnormal physical condition. The control information outputted from the control information output unit 108 is configured to be inputted to a vehicle control unit 302 of the vehicle 10. The vehicle control unit 302 is a control unit that is configured to control each unit and part of the vehicle 10, and performs a control corresponding to the control information.

(Contents of Control)

Next, contents of the control performed by the control information outputted from the control information output unit 108 (in other words, contents of the control performed by the vehicle control unit 302) will be specifically described.

The control information output unit 108 outputs, for example, the control information about autonomous driving of the vehicle 10. Specifically, the control information output unit 108 may output the control information for allowing the elimination of a low-frequency motion in a motion control unit that controls the movement of the vehicle 10. In this way, it is possible to prevent minute vibration that causes the motion sickness. The control information output unit 108 may output the control information for allowing the avoidance of sudden braking or sudden start. The control information output unit 108 may output such a control information that allows the vehicle 10 to be slowly pulled over. The control information output unit 108 may output the control information that when the vehicle 10 is running at an autonomous driving level 3 or higher (i.e., at a level where the driver is hardly involved in driving), the autonomous driving level is reduced to one of 0 to 2 (i.e., at a level where the driver is involved in driving) so that the driver can pull over.

Furthermore, the control information output unit 108 may output the control information for controlling air conditioning in a vehicle cabin. That is, it may output information for changing a state of the air in the vehicle cabin to a state in which the occupant hardly has a motion sickness. Alternatively, the control information output unit 108 may output the control information for adjusting the position of a movable navigation display unit or a movable smartphone holder in the vehicle cabin or the like at the level that outside scenery comes in sight when the occupant looks at a display screen. That is, it may output information for changing the occupant's field of view into the state in which the occupant hardly has a motion sickness.

(Technical Effect)

Next, a technical effect obtained by the physical condition abnormality determination system 1 according to the third example embodiment will be described.

As described in FIG. 13, according to the abnormal physical condition determination system 1 in the third example embodiment, it is possible to realize a situation in which the motion sickness is easily eliminated or a situation in which the motion sickness hardly occurs, by performing the control corresponding to the determination result about the motion sickness. As in the first and second example embodiments, the third example embodiment can be also applied to the motion sickness that occurs in a movable body other than the vehicle 10 or the abnormal physical condition other than the motion sickness.

Fourth Example Embodiment

Next, the abnormal physical condition determination system 1 according to a fourth example embodiment will be described with reference to FIG. 14. The fourth example embodiment is partially different from the above-described first to third example embodiments only in the configuration and operation, and is substantially the same in the other parts. Therefore, the parts that differ from the first to third example embodiments will be described in detail below, and the other overlapping parts will be omitted as appropriate.

(System Configuration)

First, an overall configuration of the abnormal physical condition determination system 1 according to the fourth example embodiment will be described with reference to FIG. 14. FIG. 14 is a block diagram illustrating the overall configuration of the abnormal physical condition determination system according to the fourth example embodiment. Incidentally, in FIG. 14, the same components as those illustrated in FIG. 1 carry the same reference numerals.

Figure 14:
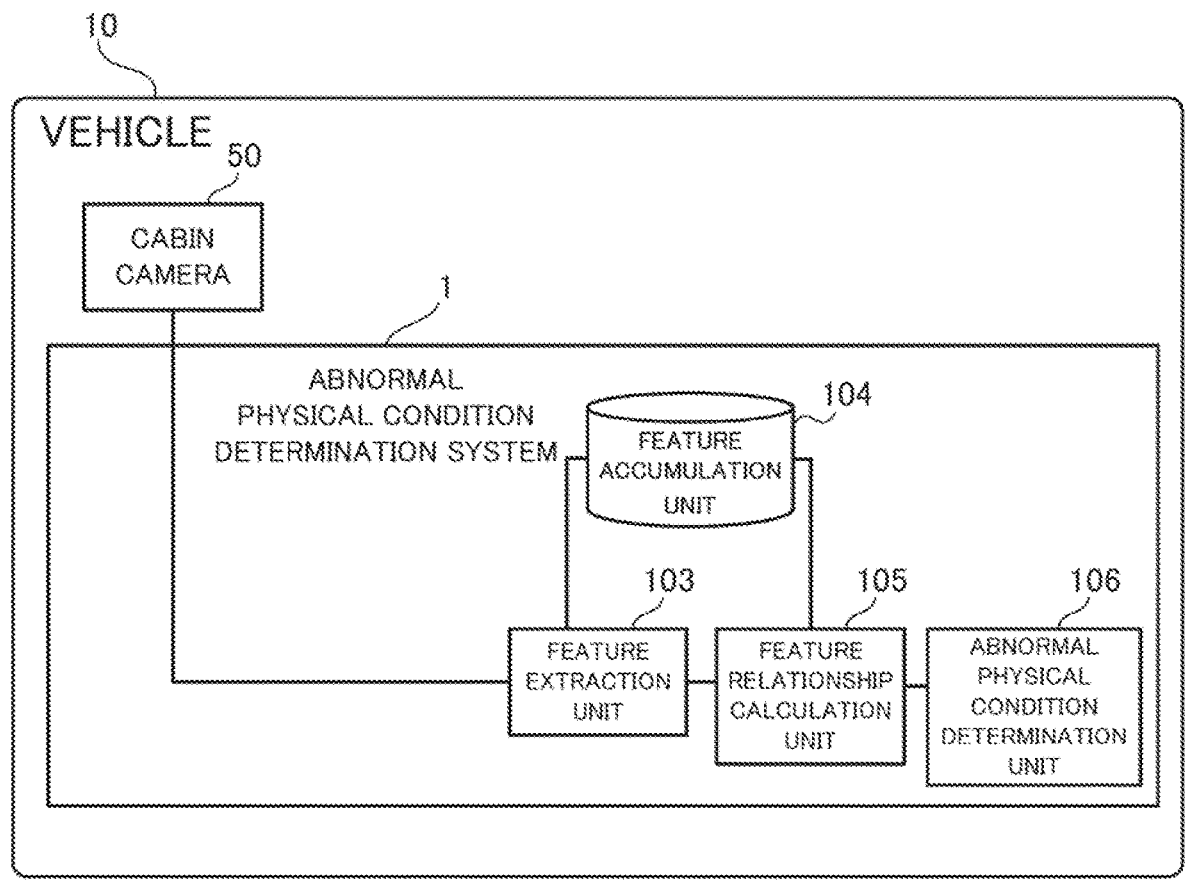
FIG. 14 is a block diagram illustrating an overall configuration of an abnormal physical condition determination system according to a fourth example embodiment.

As illustrated in FIG. 14, the abnormal physical condition determination system 1 according to the fourth example embodiment includes the feature extraction unit 103, the feature accumulation unit 104, the feature relationship calculation unit 105, and the abnormal physical condition determination unit 106. That is, the abnormal physical condition determination system 1 according to the fourth example embodiment does not include the image acquisition unit 101 and the target detection unit 102 among the components of the abnormal physical condition determination system 1 according to the first example embodiment (see FIG. 1).

The feature extraction unit 103 according to the fourth example embodiment is configured to obtain an image captured by the cabin camera 50 and to extract feature quantities for determining the abnormal physical condition of a target person from the image. The components other than the feature quantity extraction unit 103 (i.e., the feature accumulation unit 104, the feature relationship calculation unit 105, and the abnormal physical condition determining unit 106) are configured in the same manner as those in the first to third example embodiments.

Especially in the fourth example embodiment, as in the first to third example embodiments already described, the detection of the target person by the target detection unit 102 (e.g., detection of the face area of the target person, etc.) is not performed. For this reason, it is preferable that the image obtained by the feature extraction unit 103 is an image including an area suitable for extracting feature quantities (e.g., an image obtained by enlarging and imaging a facial periphery of the target person or the like). In order to capture such an image, for example, an imaging range of the cabin camera 50 may be adjusted to be an appropriate range in advance, or the cabin camera 50 may be provided with a function of automatically adjusting the imaging range. Alternatively, the feature extraction unit 103 may have a function of automatically detecting the area suitable for extracting feature quantities from the captured image and of extracting feature quantities from the area.

(Technical Effect)

Next, a technical effect obtained by the physical condition abnormality determination system 1 according to the fourth example embodiment will be described.

As described in FIG. 14, according to the abnormal physical condition determination system 1 in the fourth example embodiment, as in the first example embodiment, the motion sickness of the occupant can be determined on the basis of the relationship between each feature quantity extracted from the image of the occupant. Especially in the fourth example embodiment, since the system configuration is simplified, it is possible to suppress the cost and size of the apparatus. As in the first to third example embodiments, the fourth example embodiment can be also applied to the motion sickness that occurs in a movable body other than the vehicle 10 or the abnormal physical condition other than the motion sickness.

<Supplementary Notes>

The example embodiments described above may be described in, but not limited to, the following Supplementary Notes.

(Supplementary Note 1)

An abnormal physical condition determination system described in Supplementary Note 1 is an abnormal physical condition determination system including: an extraction unit that extracts a plurality of feature quantities indicating a condition of a target person from an image of the target person; an accumulation unit that accumulates the plurality of feature quantities as time series data; a calculation unit that calculates a relationship between each feature quantity from the plurality of feature quantities accumulated in the accumulation unit; and a determination unit that determines an abnormal physical condition of the target person on the basis of the relationship.

(Supplementary Note 2)

An abnormal physical condition determination system described in Supplementary Note 2 is the abnormal physical condition determination system described in Supplementary Note 1, wherein the calculation unit calculates the relationship from a degree of a change per unit time in the plurality of feature quantities.

(Supplementary Note 3)

An abnormal physical condition determination system described in Supplementary Note 3 is the abnormal physical condition determination system described in Supplementary Note 1 or 2, wherein the calculation unit calculates a correlation or a ratio between different feature quantities as the relationship.

(Supplementary Note 4)

An abnormal physical condition determination system described in Supplementary Note 4 is the abnormal physical condition determination system described in any one of Supplementary Notes 1 to 3, wherein the plurality of feature quantities includes feature quantities related to a position of a pupil of the target person, a direction of a face, or a gaze direction.

(Supplementary Note 5)

An abnormal physical condition determination system described in Supplementary Note 5 is the abnormal physical condition determination system described in any one of Supplementary Notes 1 to 4, wherein the relationship includes at least one of a correlation between a face position and a position of a pupil, a correlation between a face pan direction and a gaze horizontal direction, and a correlation between a face tilt direction and a gaze vertical direction.

(Supplementary Note 6)

An abnormal physical condition determination system described in Supplementary Note 6 is the abnormal physical condition determination system described in any one of Supplementary Notes 1 to 5, wherein the relationship includes at least one of a ratio in a moving velocity between a face gravity-center position and an eye position, a ratio in an angular velocity between a face pan direction and a gaze horizontal direction, and a ratio in the angular velocity between a face tilt direction and a gaze vertical direction.

(Supplementary Note 7)

An abnormal physical condition determination system described in Supplementary Note 7 is the abnormal physical condition determination system described in any one of Supplementary Notes 1 to 6, wherein the determination unit determines and outputs a degree of the abnormal physical condition on the basis of the relationship.

(Supplementary Note 8)

An abnormal physical condition determination system described in Supplementary Note 8 is the system for determining abnormal physical condition described in any one of Supplementary Notes 1 to 7, further comprising: a presentation unit that presents information about the abnormal physical condition of the target person corresponding to a determination result of the determination unit, to at least one of the target person and a person who is around the target person.

(Supplementary Note 9)

An abnormal physical condition determination system described in Supplementary Note 9 is the abnormal physical condition determination system described in any one of Supplementary Notes 1 to 8, wherein the target person is an occupant of a vehicle, and the abnormal physical condition determination system further includes an output unit that outputs a control information for controlling the vehicle in accordance with the abnormal physical condition, on the basis of a determination result of the determination unit.

(Supplementary Note 10)

An abnormal physical condition determination system described in Supplementary Note 10 is the abnormal physical condition determination system described in any one of Supplementary Notes 1 to 9, wherein the abnormal physical condition is a motion sickness.

(Supplementary Note 11)

An abnormal physical condition determination method described in Supplementary Note 11 is an abnormal physical condition determination method including: extracting a plurality of feature quantities indicating a condition of a target person from an image of the target person; accumulating the plurality of feature quantities as time series data; calculating a relationship between each feature quantity from the plurality of feature quantities accumulated in the accumulation unit; and determining an abnormal physical condition of the target person on the basis of the relationship.

(Supplementary Note 12)

A computer program described in Supplementary Note 12 is a computer program that operates a computer: to extract a plurality of feature quantities indicating a condition of a target person from an image of the target person; to accumulate the plurality of feature quantities as time series data; to calculate a relationship between each feature quantity from the plurality of feature quantities accumulated in the accumulation unit; and to determine an abnormal physical condition of the target person on the basis of the relationship.

The present invention is not limited to the examples described above and is allowed to be changed, if desired, without departing from the essence or spirit of the invention which can be read from the claims and the entire specification. An abnormal physical condition determination system, an abnormal physical condition determination method, and a computer program with such changes are also intended to be within the technical scope of the present invention.

DESCRIPTION OF REFERENCE CODES

1 Abnormal physical condition detection system
10 Vehicle
11 CPU
12 RAM
13 ROM
14 Storage apparatus
15 Input apparatus
16 Output apparatus
17 Data bus
20 External server
50 Cabin camera
101 Image acquisition unit
102 Target detection unit
103 Feature extraction unit
104 Feature accumulation unit
105 Feature relationship calculation unit
106 Abnormal physical condition determination unit
107 Determination result output unit
108 Control information output unit
201,202 Occupant
301 Display unit
302 Vehicle control unit

What is claimed is:

1. An abnormal physical condition determination system comprising:
at least one memory storing instructions; and
at least one processor configured to execute instructions to:
extract a plurality of feature quantities indicating a condition of a target person from an image of the target person;
accumulate the plurality of feature quantities as time series data in the memory;
calculate a relationship between each feature quantity from the plurality of feature quantities accumulated in the memory; and
determine an abnormal physical condition of the target person on the basis of the relationship, wherein
the relationship includes at least one of correlations between (i) a face position and a position of a pupil, (ii) a face pan direction and a gaze horizontal direction, and (iii) a face tilt direction and a gaze vertical direction, and
the abnormal physical condition of the target person is determined when at least one or more of a plurality of conditions are satisfied, including
(a) when the face position and the pupil position do not change in the same manner, (b) when the face pan direction and the gaze horizontal direction do not change in the same manner, and (c) when the face tilt direction and the gaze vertical direction do not change in the same manner.

2. The abnormal physical condition determination system according to claim 1, wherein the processor calculates the relationship from a degree of a change per unit time in the plurality of feature quantities.

3. The abnormal physical condition determination system according to claim 1, wherein the processor calculates a correlation or a ratio between different feature quantities as the relationship.

4. The abnormal physical condition determination system according to claim 1, wherein the plurality of feature quantities includes feature quantities related to a position of a pupil of the target person, a direction of a face, or a gaze direction.

5. The abnormal physical condition determination system according to claim 1, wherein the processor determines and outputs a degree of the abnormal physical condition on the basis of the relationship.

6. The system for determining abnormal physical condition according to claim 1, wherein the processor is further configured to present information about the abnormal physical condition of the target person corresponding to a determination result of the processor, to at least one of the target person and a person who is around the target person.

7. The abnormal physical condition determination system according to claim 1, wherein
the target person is an occupant of a vehicle, and
the processor is further configured to output a control information for controlling the vehicle in accordance with the abnormal physical condition, on the basis of a determination result of the processor.

8. The abnormal physical condition determination system according to claim 1, wherein the abnormal physical condition is a motion sickness.

9. An abnormal physical condition determination method performed by a computer and comprising:
extracting a plurality of feature quantities indicating a condition of a target person from an image of the target person;
accumulating the plurality of feature quantities as time series data;
calculating a relationship between each feature quantity from the plurality of feature quantities accumulated in the accumulation unit; and
determining an abnormal physical condition of the target person on the basis of the relationship, wherein
the relationship includes at least one of correlations between (i) a face position and a position of a pupil, (ii) a face pan direction and a gaze horizontal direction, and (iii) a face tilt direction and a gaze vertical direction, and
the abnormal physical condition of the target person is determined when at least one or more of a plurality of conditions are satisfied, including
(a) when the face position and the pupil position do not change in the same manner, (b) when the face pan direction and the gaze horizontal direction do not change in the same manner, and (c) when the face tilt direction and the gaze vertical direction do not change in the same manner.

10. A non-transitory recording medium storing a computer program executable by a computer to perform an abnormal physical condition determination method comprising:
- extracting a plurality of feature quantities indicating a condition of a target person from an image of the target person;
- accumulating the plurality of feature quantities as time series data;
- calculating a relationship between each feature quantity from the plurality of feature quantities accumulated in the accumulation unit; and
- determining an abnormal physical condition of the target person on the basis of the relationship, wherein
  - the relationship includes at least one of correlations between (i) a face position and a position of a pupil, (ii) a face pan direction and a gaze horizontal direction, and (iii) a face tilt direction and a gaze vertical direction, and
- the abnormal physical condition of the target person is determined when at least one or more of a plurality of conditions are satisfied, including
  - (a) when the face position and the pupil position do not change in the same manner, (b) when the face pan direction and the gaze horizontal direction do not change in the same manner, and (c) when the face tilt direction and the gaze vertical direction do not change in the same manner.

* * * * *